US008825126B2

(12) United States Patent
Murozono et al.

(10) Patent No.: US 8,825,126 B2
(45) Date of Patent: Sep. 2, 2014

(54) PROBE

(75) Inventors: Tomomi Murozono, Tokyo (JP); Iwao Takahashi, Tokyo (JP); Toru Maeda, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 103 days.

(21) Appl. No.: 13/421,768

(22) Filed: Mar. 15, 2012

(65) Prior Publication Data

US 2012/0238847 A1  Sep. 20, 2012

(30) Foreign Application Priority Data

Mar. 15, 2011  (JP) ................................. 2011-056420

(51) Int. Cl.
*A61B 5/1455* (2006.01)
*A61B 5/00* (2006.01)

(52) U.S. Cl.
CPC ........... *A61B 5/14551* (2013.01); *A61B 5/6831* (2013.01); *A61B 5/6829* (2013.01)
USPC ............................ 600/344; 600/310; 600/323

(58) Field of Classification Search
USPC .................................................. 600/310–344
See application file for complete search history.

(56) References Cited

U.S. PATENT DOCUMENTS

| | | | |
|---|---|---|---|
| 4,907,594 A | 3/1990 | Muz | |
| 5,830,135 A | 11/1998 | Bosque et al. | |
| 5,919,133 A | 7/1999 | Taylor et al. | |
| 2002/0120288 A1 | 8/2002 | Dedo | |
| 2003/0100840 A1 | 5/2003 | Sugiura et al. | |
| 2003/0171662 A1 | 9/2003 | O'Connor et al. | |
| 2006/0149149 A1 | 7/2006 | Schmid | |
| 2007/0027376 A1 | 2/2007 | Todokoro et al. | |
| 2007/0073121 A1 | 3/2007 | Hoarau et al. | |
| 2007/0219440 A1 | 9/2007 | Hannula et al. | |
| 2008/0058622 A1 | 3/2008 | Baker | |
| 2008/0076982 A1 | 3/2008 | Ollerdessen et al. | |

FOREIGN PATENT DOCUMENTS

| | | |
|---|---|---|
| CN | 1744851 A | 3/2006 |
| CN | 2897155 Y | 5/2007 |
| DE | 94 17 191 U1 | 2/1995 |
| JP | 2003-225215 A | 8/2003 |
| JP | 2006-518241 A | 8/2006 |
| JP | 2007-54594 A | 3/2007 |
| WO | 00/59374 A1 | 10/2000 |
| WO | 2010/143083 A1 | 12/2010 |

OTHER PUBLICATIONS

The extended European Search Report for related European Patent Application No. 12158731.5 dated Jun. 26, 2012.
Japanese Office Action for the related Japanese Patent Application No. 2011-056420 dated Apr. 1, 2014.
European Office Action for the related European Patent Application No. 12 158 731.5 dated Feb. 24, 2014.
Chinese Office Action for the related Chinese Patent Application No. 2012100654285 dated Mar. 13, 2014.

*Primary Examiner* — Eric Winakur
*Assistant Examiner* — Marjan Fardanesh
(74) *Attorney, Agent, or Firm* — Kenealy Vaidya LLP

(57) ABSTRACT

A probe includes: light emitting and receiving sections; an attachment band including a first surface facing the living tissue and a second surface opposite to the first surface, a part of the first surface in which one of a hook portion and a loop portion is provided, a part of the second surface in which the other is provided, the attachment band to be wrapped around the living tissue to engage the hook and loop portions with each other; and a compressible member attached to the first surface, being in contact with the living tissue when the attachment band is attached to the living tissue, the compressible member which is larger in width than the attachment band and ends of which extend beyond ends of the attachment band.

8 Claims, 4 Drawing Sheets

PROBE

BACKGROUND OF THE INVENTION

The present invention relates to a probe which is preferably used in, for example, a pulse oximeter for optically measuring the arterial oxygen saturation.

A pulse oximeter is an apparatus for measuring the arterial oxygen saturation in living tissue based on a ratio of the intensity of transmitted light which has been transmitted through the living tissue, to irradiation light which irradiates the living tissue. When measurement is to be performed, a probe including a light emitting section having a light source and a light receiving section for converting the received light to an electric signal the level of which corresponds to the intensity of the received light is attached to the finger or the like.

As such a probe, for example, there is a probe which is disclosed in JP-A-2003-225215. The probe includes a supporting member which has a substantially band-like shape in order to be wrapped around the finger or the like, and light emitting and receiving sections which are attached to the supporting member. In the state where the supporting member is wrapped around the finger or the like, the probe can be attached to the finger or the like by bonding through an adhesive surface which is provided on the supporting member.

In such a probe, in order to prevent the supporting member, which is relatively hard, from being in direct contact with the finger or the like, when the probe is attached to the finger or the like, a soft material such as a sponge is attached to a surface of the supporting member which is to be in contact with the living body. The supporting member and the sponge have a substantially same width. Depending on the manner or the place of attaching the supporting member, therefore, end portions of the supporting member may be in direct contact with the skin of the attachment place to press the place. In the case where such a probe is attached to the finger or the like of a premature infant or neonatal infant the skin of whom is weak, when the supporting member is in direct contact with the skin, particularly, there is a possibility that the skin of the attachment place is damaged.

SUMMARY

In order to achieve the object, according to the invention, there is provided a probe comprising: a light emitting section configured to emit light toward living tissue; a light receiving section configured to receive the light that is emitted from the light emitting section and that is transmitted through the living tissue; an attachment band in which the light emitting section and the light receiving section are provided, the attachment band which includes a first surface which faces the living tissue when the attachment band is attached to the living tissue, and a second surface which is opposite to the first surface, a part of the first surface in which one of a hook portion and a loop portion of a surface fastener is provided, a part of the second surface in which the other of the hook portion and the loop portion of the surface fastener is provided, the attachment band which is to be wrapped around the living tissue to engage the hook portion and the loop portion of the surface fastener with each other, thereby being attached to the living tissue; and a compressible member which is attached to the first surface of the attachment band, the compressible member which is in contact with the living tissue when the attachment band is attached to the living tissue, the compressible member which is larger in width than the attachment band and ends of which extend beyond ends of the attachment band.

The compressible member may cover end portions of the attachment band.

The attachment band may be formed by a material which is hardly extendable and contractible in a longitudinal direction.

The first surface of the attachment band may include a first portion to which the compressible member is attached, and a second portion which is different from the first portion and which is narrower in width than the first portion.

In the attachment band, a connecting portion through which an attachment portion for the light emitting section is connected to an attachment portion for the light receiving section may be narrower in width than another portion of the attachment band.

The compressible member may be a sheet-like sponge, and be placed on a light emitting surface of the light emitting section and a light receiving surface of the light receiving section.

The ends of the compressible member may include both ends in a width direction and one end in a longitudinal direction, and the ends of the attachment band may include both ends in the width direction and one end in the longitudinal direction.

The one end of the attachment band may be an end of a part of the attachment band in which the light emitting section and the light receiving section are provided.

The description does not list all the necessary features of the invention, but sub-combinations of a group of these features can also constitute the invention.

DETAILED DESCRIPTION OF EMBODIMENTS

Figure 1:
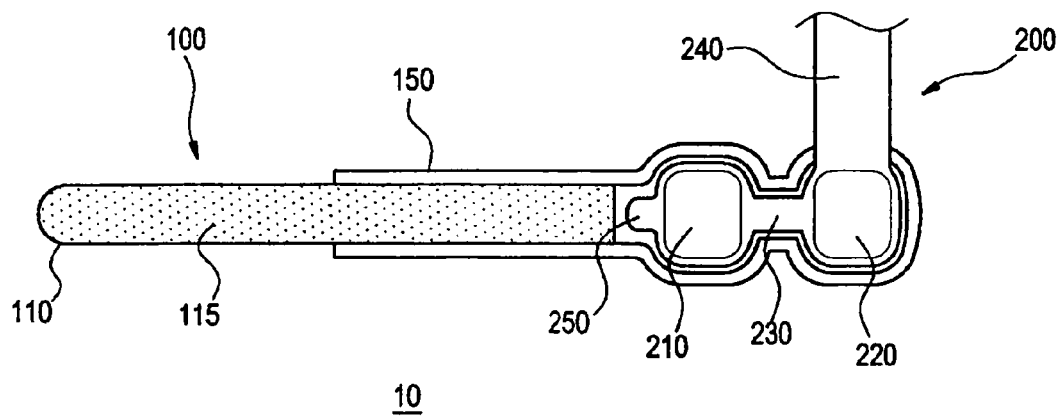
FIG. 1 is a front surface view of a probe of an embodiment of the invention.
Figure 2:
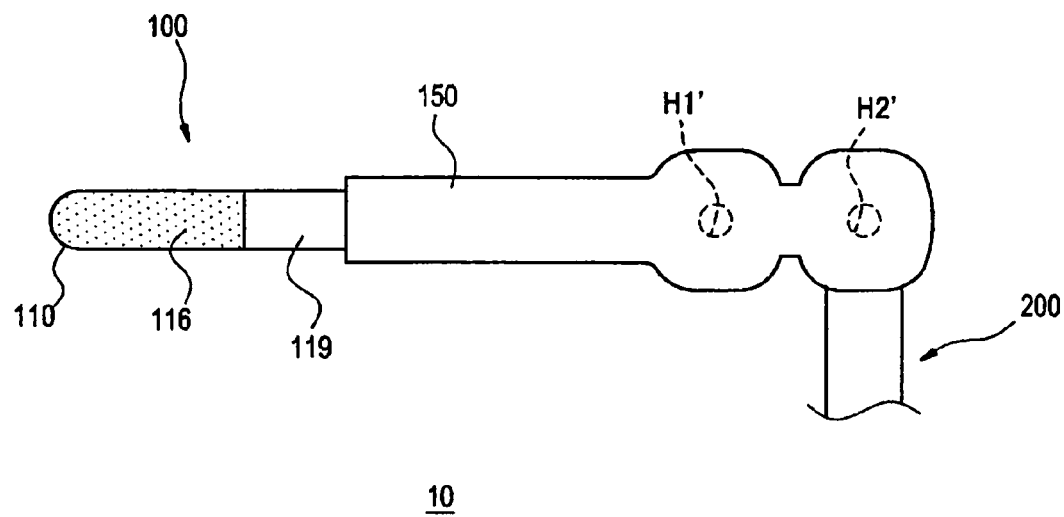
FIG. 2 is a rear surface view of the probe.
Figure 3:
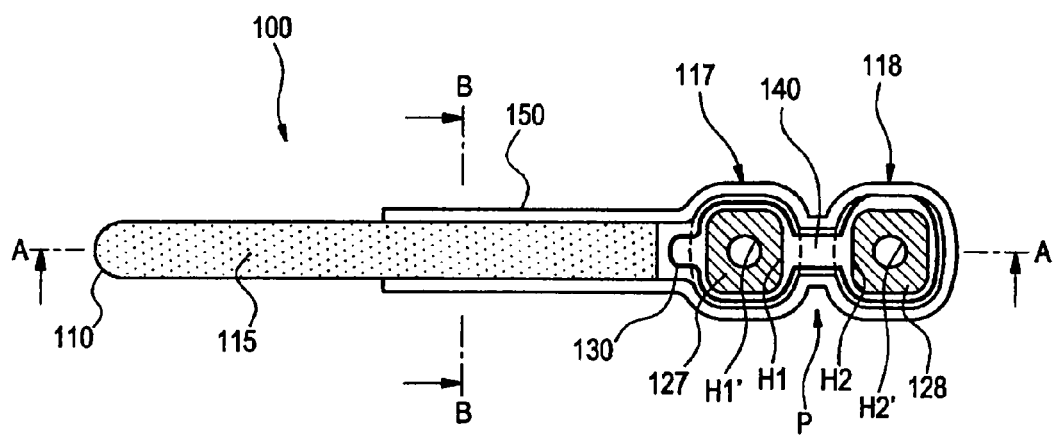
FIG. 3 is a front surface view of a band section in a state where a sensor section is detached from the probe.
Figure 4:
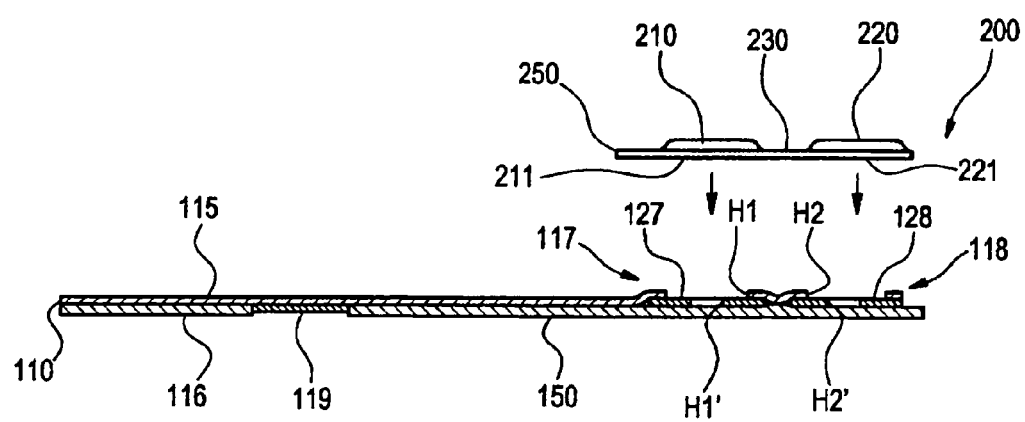
FIG. 4 is a sectional view taken along line A-A in FIG. 3.
Figure 5:
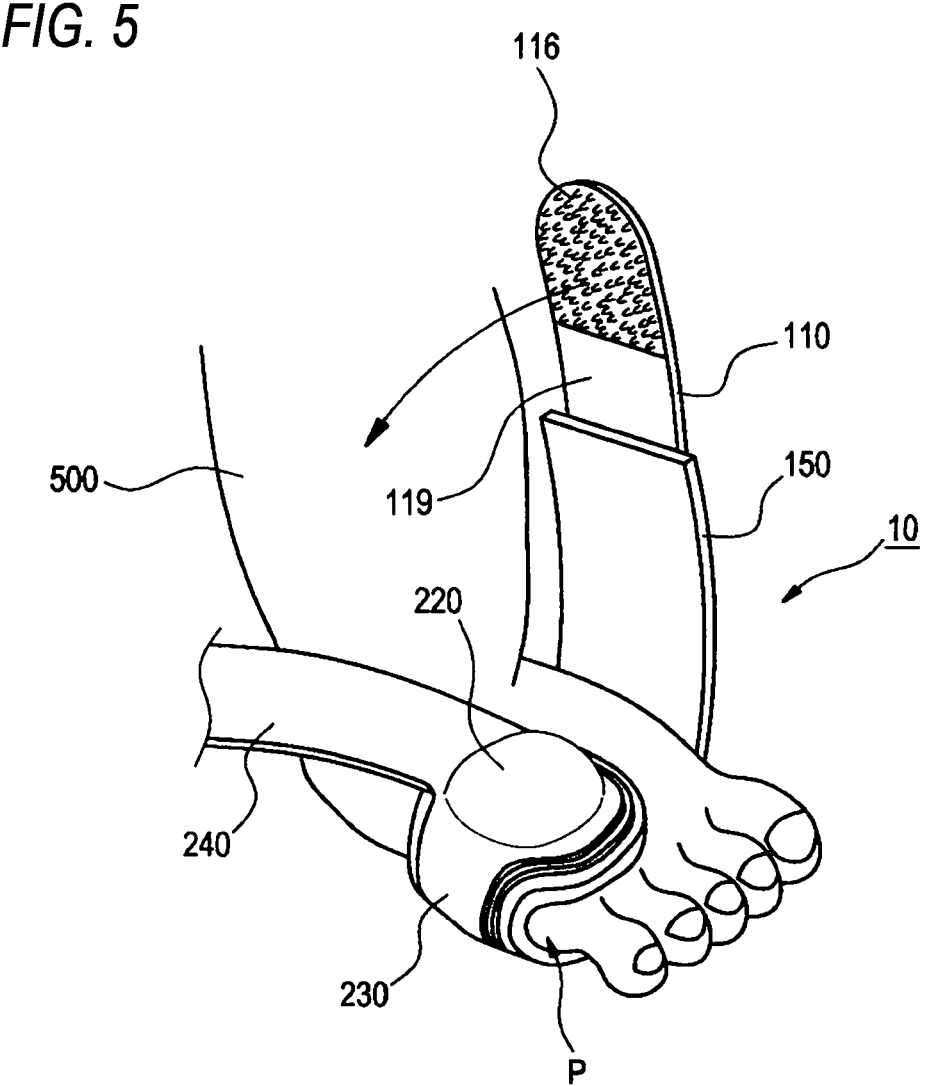
FIG. 5 is a view showing a manner of attaching the probe to the foot of a neonatal infant.
Figure 6:
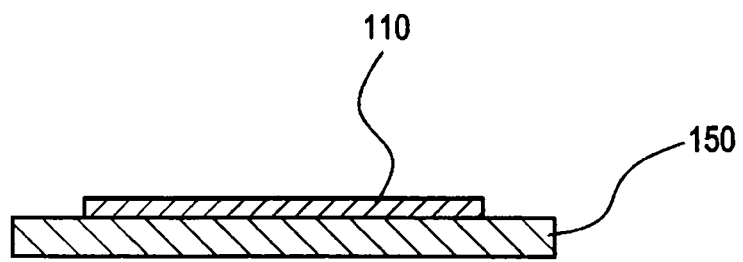
FIG. 6 is a sectional view taken along line B-B in FIG. 3.
Figure 7:
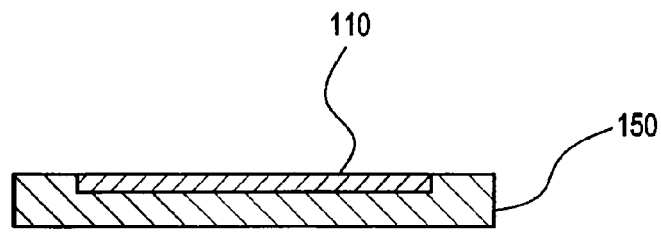
FIG. 7 is a sectional view corresponding to FIG. 6 in an example in which a sponge sheet is disposed so as to cover end portions of an attachment band.

FIG. 1 is a top view of a probe 10 of an embodiment of the invention, FIG. 2 is a rear view of the probe 10, FIG. 3 is a top view of a band section 100 in a state where a sensor section 200 is detached from the probe 10, FIG. 4 is a sectional view taken along line A-A in FIG. 3, FIG. 5 is a view showing a manner of attaching the probe 10 to the foot of a neonatal infant, FIG. 6 is a sectional view taken along line B-B in FIG. 3, and FIG. 7 is a sectional view corresponding to FIG. 6 in an example in which a sponge sheet 150 is disposed so as to cover end portions of an attachment band 110.

The probe 10 of the embodiment is preferably used in, for example, a pulse oximeter for optically measuring the arterial oxygen saturation, and includes the band section 100 and the sensor section 200. At each use of the probe, a new band section is attached to the sensor section 200 to be used as the band section 100. Each time when the patient is replaced with another patient, a new sensor section is attached to the probe to be used as the sensor section 200.

The sensor section 200 includes a light emitting section 210, a light receiving section 220, a connecting portion 230, a flexible wiring 240, and a probe tab 250. When the probe 10 is attached to living tissue such as the finger (in the example, the foot 500 of a neonatal infant), the light emitting section 210 emits light from a light emitting surface 211 shown in FIG. 4, toward the living tissue. For example, the light emitting section 210 is configured by a light emitting diode. The light receiving section 220 receives the light which is emitted from the light emitting section 210 toward the living tissue, and which is transmitted through the living tissue, through a light receiving surface 221. For example, the light receiving section 220 is configured by a photodiode.

In the sensor section 200 in the example, each of the light emitting section 210 and the light receiving section 220 is covered by a resin package except the light emitting surface 211 and the light receiving surface 221. The light emitting and receiving sections are connected to each other through the connecting portion 230. In the sensor section 200, the probe tab 250 is disposed on the side of the light emitting section 210, and functions as a pull when, for example, the sensor section 200 is to be detached from the band section 100.

The flexible wiring 240 extends in a substantially flat shape from the light receiving section 220 of the sensor section 200. The flexible wiring 240 incorporates wires through which the light emitting section 210 and the light receiving section 220 are electrically connected to the body unit of a measuring apparatus (not shown) such as a pulse oximeter, supplies an electric power required for light emission from the body unit of the measuring apparatus to the light emitting section 210, and sends a light receiving signal from the light receiving section 220 to the body unit of the measuring apparatus.

The band section 100 includes the attachment band 110 and the sponge sheet 150. The attachment band 110 is a substantially band-like member that has a flexibility that enables the band to be wrapped around living tissue to which the probe 10 is to be attached, and that is formed by a material that is hardly extendable and contractable in the longitudinal direction. As shown in FIG. 3, a light emitting section attaching portion 117 to which the light emitting section 210 of the sensor section 200 is to be attached, and a light receiving section attaching portion 118 to which the light receiving section 220 is to be attached are disposed in one end side of the surface of the attachment band.

In the light emitting section attaching portion 117, an opening H1 is disposed at a position which, when the light emitting section 210 is attached to the light emitting section attaching portion 117, is opposed to the light emitting surface 211. Also in the light receiving section attaching portion 118, an opening H2 is disposed at a position which, when the light receiving section 220 is attached to the light receiving section attaching portion 118, is opposed to the light receiving surface 221. In the light emitting section attaching portion 117, a double-sided adhesive tape 127 the external dimensions of which are larger than the dimension of the opening H1 is placed between the attachment band 110 and the sponge sheet 150. In the light receiving section attaching portion 118, a double-sided adhesive tape 128 the external dimensions of which are larger than the dimension of the opening H2 is placed between the attachment band 110 and the sponge sheet 150.

As shown in FIGS. 3 and 4, an opening H1' which is smaller than the opening H1 is disposed in the middle of the double-sided adhesive tape 127. Similarly, as shown in FIGS. 3 and 4, an opening H2' which is smaller than the opening H2 is disposed in the middle of the double-sided adhesive tape 128. In the double-sided adhesive tapes 127, 128, therefore, parts of adhesive surfaces which are opposite to the sponge sheet 150 are exposed through the openings H1, H2, respectively. When the sensor section 200 is attached to the band section 100, the light emitting section 210 and the light receiving section 220 are fixed to the light emitting section attaching portion 117 and the light receiving section attaching portion 118 by the adhesive force of the adhesive surface which is exposed through the openings H1, H2, respectively.

In the example, in the sponge sheet 150, no opening communicating with the openings H1, H1' is not provided, and no opening communicating with the openings H2, H2' is not provided. In the example, the openings H1, H2 have a substantially same size, and the openings H1', H2' have a substantially same size. The size relationships are not restricted to this as far as the openings have a size corresponding to the sizes of the light emitting surface 211 of the light emitting section 210 and the light receiving surface 221 of the light receiving section 220.

The double-sided adhesive tapes 127, 128 are colored in a chromatic color such as black, so that light emitted from the light emitting section 210 can be prevented from being scattered to the periphery, and the light receiving section 220 can be prevented from receiving light other than light emitted from the light emitting section 210. As shown in FIG. 3, a guide mark 130 is formed in the light emitting section attaching portion 117 and the light receiving section attaching portion 118 so that the user of the probe 10 can know the attaching position in the case where the light emitting section 210 and the light receiving section 220 are to be attached to the light emitting section attaching portion 117 and the light receiving section attaching portion 118, respectively.

In the example, the guide mark 130 is drawn by a thick line of a conspicuous color such as blue along the external shape formed by planar projection of the light emitting section 210 and the light receiving section 220 to the light emitting section attaching portion 117 and the light receiving section attaching portion 118, and also the external shape of the probe tab 250 disposed on the side of the light emitting section 210 of the sensor section 200 is drawn. Therefore, an attachment error such as that the light emitting section 210 is attached to the light receiving section attaching portion 118 hardly occurs.

In the front surface of the attachment band 110, a loop portion 115 of the surface fastener is disposed in an area from the end portion of the surface opposite to the side where the light emitting section attaching portion 117 and the light receiving section attaching portion 118 are disposed, to a middle portion. In the example, the loop portion 115 is formed on the whole surface of the attachment band 110. A hook portion 116 of the surface fastener is disposed in one end side of the rear surface of the attachment band 110. On the rear surface of the attachment band 110, the sponge sheet 150 is bonded in an area from a middle portion to the other end side. The sponge sheet 150 is an example of the compressible member in the invention. A nonwoven cloth 119 which is thinner than the sponge sheet 150 is disposed between the hook portion 116 and the sponge sheet 150, so that an adequate length of the sponge sheet 150 is ensured. Namely, in the case where the nonwoven cloth 119 is not disposed, when the sponge sheet 150 is excessively long, the resulting thickness in attachment of the probe is large and hence a close contact is hardly formed, and, when the sponge sheet 150 is excessively short, there is a possibility that the attachment band 110 may be in direct contact with the skin. Therefore, the nonwoven cloth 119 which is gentle to the skin, and which is thinner than the sponge sheet 150 is disposed.

The sponge sheet 150 is larger in width than the attachment band 110, and the ends of the sponge sheet 150 extend beyond the ends of the attachment band 110 in the width direction to the outer side. In addition, the end of the sponge sheet 150 extends beyond the end of the attachment band 110 in the longitudinal direction, which is the end of the light receiving section attaching portion 118, to the outer side. In the attachment band 110, as shown in FIGS. 1 to 3, namely, the end portions are not exposed to the lateral side in the portion where the sponge sheet 150 is attached to the rear surface, including the light emitting section attaching portion 117 and the light receiving section attaching portion 118.

The sponge sheet 150 is placed also on the light emitting surface 211 of the light emitting section 210 and the light receiving surface 221 of the light receiving section 220. As shown in FIGS. 2 and 4, namely, the sponge sheet 150 is disposed so as to cover the openings H1, H1' and the openings H2, H2'.

As shown in FIG. 3, moreover, a connecting portion 140 between the light emitting section attaching portion 117 and the light receiving section attaching portion 118 in the attachment band 110 is narrower in width than the other portion of the attachment band 110. As shown in FIG. 1, a connecting portion 230 through which the light emitting section 210 and light receiving section 220 of the sensor section 200 are connected to each other is placed along the connecting portion 140 of the attachment band 110. Similarly with the connecting portion 140 of the attachment band 110, the connecting portion 230 is narrower in width than the light emitting section 210 and light receiving section 220 which are on the both sides, respectively, and further narrower in width than the connecting portion 140 of the attachment band 110.

In the sponge sheet 150, as shown in FIGS. 1 to 3, also the portion which is attached to the rear surface of the connecting portion 140 of the attachment band 110 is narrower in width than the other portion. In the probe 10 of the example, therefore, the portion between the light emitting section 210 and the light receiving section 220, i.e., the connecting portion 140 of the attachment band 110 and the connecting portion 230 (the portion denoted by "P" in FIGS. 3 and 5) of the sensor section 200 have a shape which is constricted in the both sides in the width direction.

When the thus configured probe 10 is to be attached to, for example, the foot 500 of a neonatal infant as shown in FIG. 5, the light emitting section 210 and the light receiving section 220 are placed so that the light emitting surface 211 of the light emitting section 210 and the light receiving surface 221 of the light receiving section 220 are placed on the sole and instep of the foot 500 so as to be opposed to each other. Then, the band section 100 is wrapped while the rear surface side (the side to which the sponge sheet 150 is attached) of the attachment band 110 buts against the foot 500 of the neonatal infant. Thereafter, the hook portion 116 of the surface fastener which is disposed on the rear surface of the attachment band 110 is caused to butt against the loop portion 115 of the surface fastener which is disposed on the front surface of the attachment band 110, whereby the band section 100 is fixed to the foot 500 of the neonatal infant in a state where it is wrapped around the foot.

In the probe 10 of the example, as described above, the sponge sheet 150 is larger in width than the attachment band 110 and the ends of the sponge sheet 150 extend beyond the ends of the attachment band 110 to the outer side. In attachment of the probe 10, therefore, the foot 500 of the neonatal infant is not directly pressed by the end portions of the attachment band 110. Also after attachment of the probe 10, similarly, only the sponge sheet 150 of the probe 10 is in direct contact with the foot 500 of the neonatal infant, and hence the attachment band 110 does not directly press the foot 500 of the neonatal infant.

The probe 10 of the example can be fixed by the surface fastener including the loop portion 115 and the hook portion 116. As compared with the mode where the fixation is performed by an adhesive tape or the like, consequently, there is less possibility that, in attachment, the attachment band 110 is fixed by applying an excessive force. As compared with the mode where the fixation is performed by an adhesive tape or the like, even when attachment and detachment are repeated, moreover, the engaging force is not reduced. The engaging force can be adjusted by adequately selecting the loop portion 115 and the hook portion 116 in accordance with the kind of the attachment object.

In the probe 10 of the example, the flexible wiring 240 is used as the wiring for connecting the sensor section 200 to the body unit of the measuring apparatus. Therefore, there is less possibility that, for example, the wiring bites into the surface of living tissue in attachment of the probe 10 to press the living tissue.

The section in the width direction of the probe 10 of the example has a shape shown in FIG. 6. Alternatively, as shown in a corresponding sectional shape in FIG. 7, for example, the sponge sheet 150 may be disposed so as to cover the end portions of the attachment band 110. According to the configuration, it is possible to more surely prevent the end portions in the width direction of the attachment band 110 from being in direct contact with the surface of the foot 500 of the neonatal infant.

In the probe 10 of the example, the sponge sheet 150 is disposed so as to cover the openings H1, H2. As compared with the mode where openings for causing the openings H1, H1' and H2, H2' to penetrate to the rear surface are disposed in the sponge sheet 150, therefore, there is no possibility that hole edges locally press the skin of the foot 500 of the neonatal infant. The sponge sheet 150 has a constant optical transparency, and is very thin in at least the portions covering the openings H1, H2. Therefore, most of the light emitted from the light emitting section 210, and that incident on the light receiving section 220 can be transmitted through the sponge sheet without being blocked thereby.

In the probe 10 of the example, the portion between the light emitting section 210 and the light receiving section 220 has a shape which is constricted in the both sides in the width direction. Therefore, the attachment band 110 and the sponge sheet 150 can be easily bent in this portion.

In the probe 10 of the example, the attachment band 110 is formed by the material which is hardly extendable and contractible in the longitudinal direction. As compared with the case the probe is formed by an extendable and contractible material, therefore, there is no possibility that, in attachment of the probe 10, the attachment band 110 presses the skin by the contraction force of the attachment band 110.

In the probe 10 of the example, the nonwoven cloth 119 which is thinner than the sponge sheet 150 is disposed between the hook portion 116 and the sponge sheet 150. As compared with the mode where the nonwoven cloth 119 is not disposed, therefore, it is possible to more surely prevent the attachment band 110 from being in direct contact with the skin. As compared with the mode where the sponge sheet 150 extends to the boundary with the hook portion 116, moreover, the probe can be easily attached.

Figure 8:
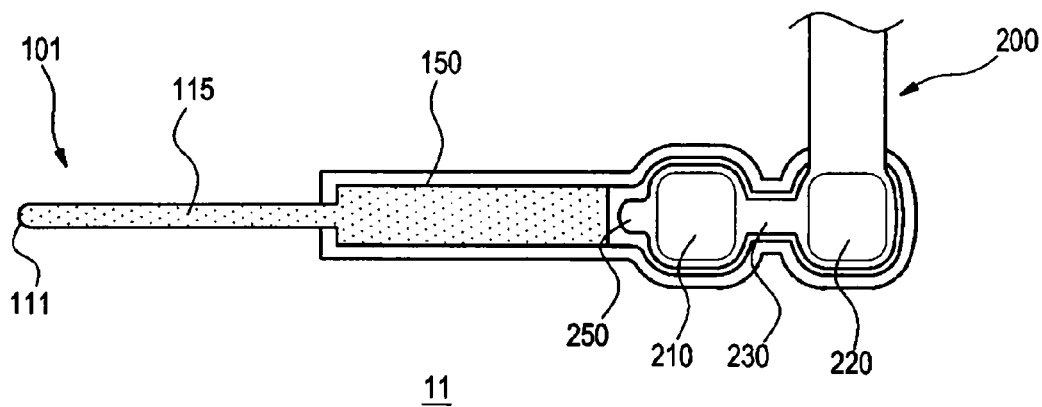
FIG. 8 is a front surface view of a probe of another example of the embodiment of the invention.
Figure 9:
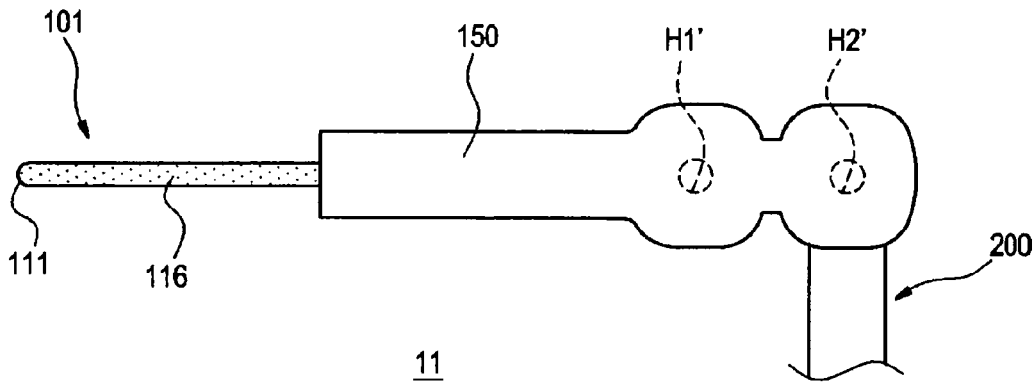
FIG. 9 is a rear surface view of the probe.

FIG. 8 is a top view of a probe 11 of another example of the embodiment of the invention, and FIG. 9 is a rear surface view of the probe 11. In the probe 11 of the example, components which are identical with those of the above-described probe 10 are denoted by the same reference numerals, and their description is omitted.

The probe 11 of the example includes a band section 101 including an attachment band 111 in place of the attachment band 110 of the probe 10, and the sensor section 200. In the attachment band 111, the portion where the sponge sheet 150 is not attached to the rear surface is narrower in width than that where the sponge sheet 150 is attached. According to the configuration, even in the case where the attachment band 111 is fixed in a state where it is laterally deviated, the end portions in the width direction of the attachment band 111 are hardly protruded toward the outside from the end portions in the width direction of the sponge sheet 150, and hence it is possible to more surely prevent the end portions in the width direction of the attachment band 111 from being in direct contact with the living body surface.

According to an aspect of the invention, it is possible to surely prevent the end portions in the width direction of the attachment band from being in direct contact with the living tissue. Therefore, there is no possibility that the skin of the attachment place of the probe is damaged. The probe can be fixed by the surface fastener. As compared with the mode where the fixation is performed by an adhesive tape or the like, consequently, there is less possibility that, in attachment, the attachment band is fixed by applying an excessive force. Moreover, as compared with the mode where the fixation is performed by an adhesive tape or the like, the engaging force is not reduced even when attachment and detachment are repeated.

According to an aspect of the invention, the compressible member is disposed so as to cover the end portions of the attachment band, thus it is possible to more surely prevent the end portions in the width direction of the attachment band from being in direct contact with the living tissue.

When the member which is to be wrapped around the finger or the like is formed by a material which is expandable and contractible, there is a possibility that, in attachment of the probe, the member is caused to press the skin of the attachment place by the contraction force of the member which is caused by fixation of the member in a state where it is extended. According to an aspect of the invention, the attachment band is formed by the material which is hardly extendable and contractible in the longitudinal direction, so that, there is no possibility that, in attachment of the probe, the attachment band presses the skin by the contraction force such as described above.

According to an aspect of the invention, in the surface of attachment band opposed to the living tissue, the width of the portion in which the compressible member is not attached is made narrower than that of the portion in which the compressible member is attached. Even when the attachment band is fixed in a state where it is laterally deviated in the width direction, the end portions in the width direction of the attachment band are hardly protruded to the outside beyond those in the width direction of the compressible member. Therefore, it is possible to more surely prevent the end portions in the width direction of the attachment band from being in direct contact with the living body.

According to an aspect of the invention, in the attachment band, the width of the connecting portion through which the attachment portion for the light emitting section is connected to that for the light receiving section is made narrower than the width of the other portion. When the probe is attached so that the light emitting and receiving sections are placed on the instep and sole of the foot of a neonatal infant, for example, the connecting portion is placed on the lateral side of the foot.

In this case, the attachment band can be easily bent in the connecting portion because the width of the connecting portion is narrow.

According to an aspect of the invention, the compressible member is formed by a sheet-like sponge, and covers the light emitting surface of the light emitting section and the light receiving surface of the light receiving section. In this configuration, as compared in the mode where holes are disposed respectively on the light emitting and receiving surfaces, there is no possibility that hole edges locally press the skin of a neonatal infant. Since the compressible member is formed by a sheet-like sponge, light emitted from the light emitting section, and that incident on the light receiving section can be transmitted through the member. It is a matter of course that the compressible member which covers the light emitting surface of the light emitting section and the light receiving surface of the light receiving section have a thickness that enables most of light emitted from the light emitting section, and that incident on the light receiving section to be transmitted therethrough without being blocked thereby.

Although the invention has been described using the embodiment, the technical scope of the invention is not restricted to the scope of the description of the embodiment. It is obvious to those skilled in the art that various changes or improvements can be made on the embodiment. It is obvious from the definition of the appended claims that also embodiments in which such changes or improvements are made belong to the technical scope of the invention.

In the probes 10, 11, for example, the sponge sheet 150 is used as an example of the compressible member. Alternatively, urethane or the like may be used in place of the sponge sheet 150. The length of the portion which is in the rear surface of the attachment band 110 of the probe 10 or 11, and to which the sponge sheet 150 is not attached is not limited to the above example, and may be set to a desired value while considering the attachability or the like.

What is claimed is:
1. A probe comprising:
a light emitting section configured to emit light toward living tissue;
a light receiving section configured to receive the light that is emitted from the light emitting section and that is transmitted through the living tissue;
an attachment band having ends in a width direction, in which the light emitting section and the light receiving section are provided, the attachment band which includes a first surface which faces the living tissue when the attachment band is attached to the living tissue, and a second surface which is opposite to the first surface, a part of the first surface in which one of a hook portion and a loop portion of a surface fastener is provided, a part of the second surface in which the other of the hook portion and the loop portion of the surface fastener is provided, the attachment band which is to be wrapped around the living tissue to engage the hook portion and the loop portion of the surface fastener with each other, thereby being attached to the living tissue; and
a compressible member having ends in a width direction and which is attached to the first surface of the attachment band, the compressible member which is in contact with the living tissue when the attachment band is attached to the living tissue, wherein the compressible member is larger in width than the attachment band and ends of which extend beyond ends of the attachment band, and the ends of the attachment band are not exposed to a lateral side of the compressible member in a portion where the compressible member is attached to the first surface of the attachment band.

2. The probe according to claim 1, wherein the compressible member covers end portions of the attachment band.

3. The probe according to claim 1, wherein the attachment band is formed by a material which is hardly extendable and contractible in a longitudinal direction.

4. The probe according to claim 1, wherein the first surface of the attachment band includes a first portion to which the compressible member is attached, and a second portion which is different from the first portion and which is narrower in width than the first portion.

5. The probe according to claim 1, wherein, in the attachment band, a connecting portion through which an attachment portion for the light emitting section is connected to an attachment portion for the light receiving section is narrower in width than another portion of the attachment band.

6. The probe claim 1, wherein the compressible member is a sheet-like sponge, and is placed on a light emitting surface of the light emitting section and a light receiving surface of the light receiving section.

7. The probe according to claim 1, wherein the ends of the compressible member include both ends in a width direction and one end in a longitudinal direction, and the ends of the attachment band include both ends in the width direction and one end in the longitudinal direction.

8. The probe according to claim 7, wherein the one end of the attachment band is an end of a part of the attachment band in which the light emitting section and the light receiving section are provided.

* * * * *